United States Patent [19]

Sekhar

[11] 4,046,915
[45] Sept. 6, 1977

[54] PROCESS FOR TREATING ELEVATED PLATELET ADHESIVENESS

[75] Inventor: Neel C. Sekhar, Portage, Mich.

[73] Assignee: The Upjohn Company, Kalamazoo, Mich.

[21] Appl. No.: 717,841

[22] Filed: Aug. 26, 1976

Related U.S. Application Data

[60] Division of Ser. No. 530,255, Dec. 6, 1974, Pat. No. 3,996,103, which is a continuation of Ser. No. 371,033, June 18, 1973, abandoned, which is a continuation-in-part of Ser. No. 276,698, July 31, 1972, abandoned.

[51] Int. Cl.$^2$ .............................................. A61K 31/19
[52] U.S. Cl. ................................. 424/317; 424/304; 424/308; 424/309
[58] Field of Search .......................................... 424/317

[56] References Cited

U.S. PATENT DOCUMENTS

| | | | |
|---|---|---|---|
| 3,644,479 | 2/1972 | Judy et al. .............................. | 424/317 |
| 3,663,627 | 5/1972 | Judy et al. ........................ | 260/618 F |

Primary Examiner—Jerome D. Goldberg
Attorney, Agent, or Firm—John J. Killinger; Roman Saliwanchik

[57] ABSTRACT

A process for inhibiting platelet aggregation by the addition of a member selected from the group consisting of a compound of the formula:

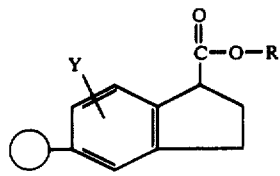

Formula 1 wherein ◯ is cyclohexane or phenyl; Y is hydrogen, halogen —CF$_3$, —OH, lower alkyl of 1 to 8 carbon atoms, lower alkoxy of 1 to 8 carbon atoms, —CN, —NH$_2$. —SH, or —S-lower alkyl of 1 to 8 carbon atoms; and R is hydrogen, lower alkyl of 1 to 8 carbon atoms, inclusive, or a pharmacologically acceptable cation, to in vivo and in vitro platelet systems. In vitro systems include whole blood as kept in blood banks, whole blood as used in heart-lung machines, and platelet-rich concentrates. In vivo systems include human or animal bodies. The process provides a means for treating hemorrhage due to thrombocytopenia which in turn is caused by irradiation, cancer chemotherapy, or immunosuppressants as well as hemophilia due to cogenital defects.

4 Claims, No Drawings

PROCESS FOR TREATING ELEVATED PLATELET ADHESIVENESS

CROSS REFERENCE TO RELATED APPLICATIONS

This application is a division of application Ser. No. 530,255, filed Dec. 6, 1974, now U.S. Pat. No. 3,996,103 which is a continuation of application Ser. No. 371,033, filed June 18, 1973, now abandoned which is a continuation-in-part of application Ser. No. 276,698, filed July 31, 1972, now abandoned.

BRIEF DESCRIPTION OF THE INVENTION

This invention relates to the prevention of platelet aggregation or thrombus formation by the addition of a compound of the Formula 1 to the plasma surrounding the platelets.

DETAILED DESCRIPTION OF THE INVENTION

The compounds of the Formula 1 are old compounds known in the art. The compounds are depicted in the protonated or acid form, however, for the purposes of the instant invention the proton can be replaced by any pharmacologically acceptable cation.

For in vivo applications the compositions of the present invention are presented for administration to humans and animals in unit dosage forms, such as tablets, capsules, pills, powders, granules, sterile parenteral solutions or suspensions, and oral solutions or suspension, and oil-in-water and water-in-oil emulsions containing suitable quantities of the compound of Formula 1.

For oral administration either solid or fluid unit dosage forms can be prepared. For preparing solid compositions such as tablets, the compound of Formula 1 is mixed with conventional ingredients such as talc, magnesium stearate, dicalcium phosphate, magnesium aluminum silicate, calcuim sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The watersoluble forms can be dissolved in an aqueous vehicle together with sugar, aromatic flavoring agents and preservatives to form a syrup. An elixir is prepared by using a hydroalcoholic (ethanol) vehicle with suitable sweeteners such as sugar and saccharin, together with an aromatic flavoring agent.

Suspensions can be prepared with a syrup vehicle with the aid of a suspending agent such as acacia, tragacanth, methylcellulose and the like.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampul and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

For in vitro applications, aqueous solutions are prepared by dissolving a compound of the Formula 1 in water and adding salt to provide an isotonic solution and buffering to a pH compatible with blood.

Advantageously the composition prepared for parenteral administration can be used when prepared omitting the local anesthetic.

The dosage for humans and animals depends on the blood volume and condition of the subject. A dosage schedule of from about 0.1 to about 300 mg. per dose administered 1 to 3 times daily is effective for reducing platelet aggregation in the subject. Expressed in terms of weight, the dose can be from 0.001 to 4.25 mg./kg./day.

For in vitro, dosage is from 0.01 to 50 micrograms/ml. of whole blood.

The compounds of the Formula 1 have an asymetric carbon atom and can exist as optical isomers.

The compounds of the Formula 1 are depicted in the protonated or acid form. However, for the purposes of the instant invention, the proton can be replaced by any pharmacologically acceptable anion. These salts can be prepared in a manner analogous to the method disclosed in Netherlands Pat. No. 66 08098 (Derwent No. 24299) and can be for example those of alkali metals and alkaline earth bases, such as sodium, potassium, calcium, and magnesium; those of ammonia or a basic amine such as mono-, di-, and triethylamines, benzylamine, heterocyclic amines such as piperidine and morpholine and amines containing water-solubilizing or hydrophilic groups such as triethanolamine and phenylmonoethanolamine such as are disclosed in U.S. Pat. No. 3,296,091. Carboxylate esters such as methyl, ethyl, cyclohexyl and the like having no more than eight carbon atoms are formed by the usual method, e.g., reaction with diazomethane or similar diazohydrocarbons as in U.S. Pat. No. 3,296,091.

The addition of compounds of the Formula 1 to whole blood provide in vitro applications of the invention such as in the storage of whole blood in blood banks, and whole blood to be used in heart-lung machines. Additionally, whole blood containing a compound of the Formula 1 can be circulated through organs, e.g., heart and kidneys, which have been removed from a cadaver and prior to transplant.

The compounds of the Formula 1 can also be used for the preparation of stable platelet-rich plasma concentrates in the same manner as the prostaglandins as disclosed in U.S. Pat. No. 3,629,071 and Science, Vol. 175, pp. 536 –542 (Feb. 4, 1972).

In vivo applications are the administration to humans and animals to prevent clot formation in situations such as following surgery to prevent postoperative thrombosis; in geriatric patients to prevent transient cerebral ischemic attacks; and long-term prophylaxis following myocardial infarcts and strokes.

In general a compound of the Formula 1 is usefully administer prophylactically to humans having a platelet adhesiveness value in excess of 25% [Bygdeman et al., J. Atheroscler. Res., 10, 33-39 (1969) ].

EXAMPLE 1

A lot of 10,000 tablets, each containing 0.1 mg. of 5-phenyl-1-indancarboxylic acid is prepared from the following types and amounts of ingredients:

| 5-phenyl-1-indancarboxylic acid | 1 gm. |
|---|---|
| Dicalcium phosphate | 1,500 gm. |
| Methylcellulose, U.S.P. (15 cps.) | 60 gm. |
| Talc | 150 gm. |
| Corn starch | 200 gm. |
| Calcium stearate | 12 gm. |

The dicalcium phosphate and active ingredient are mixed well, granulated with 7.5 percent solution of methylcellulose in water, passed through a No. 8 screen and dried carefully. The dried granules are passed through a No. 12 screen, mixed thoroughly with the talc, starch and magnesium stearate, and compressed into tablets.

These tablets are useful in preventing thrombus formation at a dose of 1 tablet every four hours following surgery.

EXAMPLE 2

One thousand two-piece hard gelatin capsules, each containing 100 mg. of 5-phenyl-1-indancarboxylic acid are prepared from the following types and amounts of ingredients:

| 5-phenyl-1-indancarboxylic acid | 100 gm. |
|---|---|
| Talc | 100 gm. |
| Magnesium stearate | 10 gm. |

The ingredients are mixed well and filled into capsules of the proper size.

Capsules so prepared are useful in preventing further coronary infarcts at a dose of one capsule daily to a patient recovering from a coronary infarct.

EXAMPLE 3

One thousand tablets, each containing 100 mg. of 5-phenyl-1-indancarboxylic acid are made from the following types and amounts of ingredients:

| 5-phenyl-1-indancarboxylic acid | 100 gm. |
|---|---|
| Microcrystalline cellulose NF | 120 gm. |
| Starch | 16 gm. |
| Magnesium stearate powder | 4 gm. |

The ingredients are screened and blended together and pressed into 240 mg. tablets.

The tablets are useful to protect against transient cerebral ischemic attacks at a dose of one tablet daily.

EXAMPLE 4

A sterile preparation suitable for intramuscular injection and containing 1 mg. of 5-phenyl-1-indancarboxylic acid sodium salt in each milliliter is prepared from the following ingredients:

| 5-phenyl-1-indancarboxylic acid sodium salt | 1.4 gm. |
|---|---|
| Benzyl benzoate | 200 ml. |
| Methylparaben | 1.5 gm. |
| Propylparaben | 0.5 gm. |
| Cottonseed oil q.s. | 1,000 ml. |

One milliliter of this sterile preparation is injected for prophylactic treatment prior to surgery.

EXAMPLE 5

Aqueous Solution

Six hundred ml. of an aqueous solution containing 0.1 mg. of the tris(hydroxymethyl)aminomethane (THAM) salt of 5-phenyl-1-indancarboxylic acid per ml. is prepared as follows:

| Tris(hydroxymethyl)aminomethane salt of 5-phenyl-1-indancarboxylic acid | 60 mg. |
|---|---|
| Sodium chloride | 5,400 mg. |
| Water for injection q.s. | 600 ml. |

The THAM salt and sodium chloride are dissolved in sufficient water to make 600 ml. and sterile filtered.

The solution is added to whole blood 16.0 ml./liter for use in a heart-lung machine.

EXAMPLE 6

Following the procedure of the preceding examples 1 through 7, inclusive, compositions are similarly prepared substituting an equimolar amount each of 5-cyclohexyl-1-indancarboxylic acid, 6-chloro-5-cyclohexyl-1-indancarboxylic acid and 6-chloro-5-phenyl-1-indancarboxylic acid for the acid of the previous examples.

I claim:

1. A process for treating elevated platelet adhesiveness comprising the administration of an effective amount for reducing platelet adhesiveness of a compound of the formula:

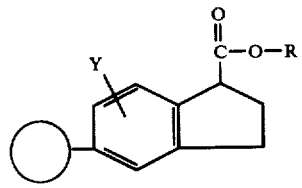

wherein ○ is phenyl; Y is hydrogen, halogen, —CF₃, —OH, lower alkyl of 1 to 8 carbon atoms, lower alkoxy of 1 to 8 carbon atoms, —NH₂, —SH, or —S-lower alkyl of 1 to 8 carbon atoms; and R is hydrogen, or a pharmacologically acceptable cation, to a human or animal having elevated platelet adhesiveness.

2. The process of claim 1 wherein the amount of the compound administered is from about 0.1 to 300 mg.

3. The process of claim 1 wherein the compound added is 5-phenyl-1-indancarboxylic acid.

4. The process of claim 1 wherein the compound added is 6-chloro-5-phenyl-1-indancarboxylic acid.

* * * * *